(12) United States Patent
Koivisto et al.

(10) Patent No.: US 6,398,549 B1
(45) Date of Patent: Jun. 4, 2002

(54) IMAGING MEANS AND DENTAL UNIT

(75) Inventors: Juha Koivisto; Christian De Godzinsky, both of Helsinki (FI)

(73) Assignee: Planmeca Oy, Helsinki (FI)

( * ) Notice: Subject to any disclaimer, the term of this patent is extended or adjusted under 35 U.S.C. 154(b) by 0 days.

(21) Appl. No.: 09/555,298

(22) PCT Filed: Nov. 27, 1998

(86) PCT No.: PCT/FI98/00930

§ 371 (c)(1),
(2), (4) Date: Sep. 5, 2000

(87) PCT Pub. No.: WO99/27865

PCT Pub. Date: Jun. 10, 1999

(30) Foreign Application Priority Data

Nov. 28, 1997 (FI) .................................................. 974365

(51) Int. Cl.⁷ .............................. A61C 1/00; A61C 3/00
(52) U.S. Cl. ........................................... 433/29; 433/27
(58) Field of Search ........................... 433/27, 28, 29, 433/215, 229

(56) References Cited

U.S. PATENT DOCUMENTS 4,900,252 A * 2/1990 Liefke et al. ................. 433/27
5,538,423 A * 7/1996 Coss et al. .................... 433/27
5,634,790 A  6/1997 Pathmanabhan et al. ...... 433/29

FOREIGN PATENT DOCUMENTS

| DE | 4009439 | 9/1991 |
| EP | 0326497 | 2/1989 |
| EP | 0678280 | 10/1995 |
| WO | 9100067 | 1/1991 |

* cited by examiner

Primary Examiner—Nicholas D. Lucchesi
(74) Attorney, Agent, or Firm—Steinberg & Raskin, P.C.

(57) ABSTRACT

The invention relates to an imaging means (10) suitable for recording images from the teeth and the mouth region. The imaging means (10) comprise an image-recording device such as a video camera, the optical components of an object illumination system, an instrument connection cable and a connector. The invention further concerns a dental unit (30) having one or more instrument connectors (C) onto which the control system of said dental unit (30) switches the physical variables required for the use of the instrument attached to said instrument connector. The invention also concerns a method of connecting an imaging means to a dental unit.

21 Claims, 4 Drawing Sheets

IMAGING MEANS AND DENTAL UNIT

FIELD OF THE INVENTION

The present invention relates to an imaging means particularly for recording images from the teeth and the mouth region, said imaging means comprising an image-recording device such as a video camera, an object illumination system, optical elements, an instrument connection cable and a connector.

The invention also concerns a dental unit including at least one instrument connector, whereby the control system of the dental unit steers the physical variables related to the use of an instrument attached to said instrument connector. The invention further concerns a method of connecting an imaging means to a dental unit.

BACKGROUND OF THE INVENTION

An intraoral camera is an imaging means based on video image recording, most generally used by a dentist as an accessory for imaging the teeth and the mouth region and making a diagnosis on these anatomic regions. An intraoral camera facilitates accurate imaging of a single tooth, a part thereof or any other region of the mouth, complemented with a full-face picture. Pictures taken with an intraoral camera can be recorded in a storage means and, with the help of the stored pictures, the outcome of the care can be elucidated by comparing pictures taken before and after the care. In conjunction with an ongoing care, the intraoral camera can be utilized for showing the patient a specific part of the mouth needing care, thus motivating the necessity of the care for the patient.

In conventional intraoral camera systems, the imaging means comprises a base unit and a hand-held imaging instrument, later in the text called a camera handpiece. The base unit typically includes a power supply, a control electronics unit and a light source. Further there is required a video monitor for displaying the image and possibly storage means for archiving the pictures. Light generated by the light source is generally taken from the base unit to the camera handpiece along a light guide. Typically, the video camera circuitry is located in the base unit and the light-sensitive image sensor element in the handpiece. During an imaging session, the tip of the camera handpiece with its light output exit is taken close to the object to be imaged and the image is projected via the imaging optics onto the light-sensitive image sensor and further in an electrical format to the video camera electronics, and therefrom as a video signal to a display or storage means.

To avoid deterioration of image quality due to shadows, the illumination of the object to be viewed by an intraoral camera must be made as uniform as possible. Generally, light is launched onto the viewed object from the tip of the camera handpiece via an annular light output exit adapted to surround the imaging optics. The better the object illumination the smaller lens aperture of the video camera optics can be used, whereby the depth of field of view can be extended. Particularly for dental imaging, a large depth of field is an essential factor contributing to both the ease of operation and quality of imaging inasmuch the need for constant refocusing is eliminated.

Generally, an intraoral camera system comprises a separate, bulky base unit which causes problems to the positioning of the unit in the frequently operating premises of a dentist. In conventional imaging means, the object illumination systems are very complicated inasmuch the light is transferred from the base unit along an optical light guide to the tip of the camera handpiece, whereby a considerable faction of the light source output is lost on the light mission path. Frequently, the output intensity of light exiting from the tip of the handpiece is insufficient to achieve a satisfactory depth of field. Moreover, the optical fiber extended from the base unit to the handpiece is subject to damage and makes the connection cable thick and stiff, whereby the handpiece located at the end of the connection cable becomes difficult to handle.

The problems associated with a separate base unit can be overcome by connecting the intraoral camera directly to the dental unit, whereby the existing functions of the dental unit can be utilized for the control of the imaging means. E.g., patent publications EP 678 280 and DE 40 09 439 disclose embodiments in which the equipment manufacturer has already reserved one or a given number of instrument places on the dental unit console for connecting the imaging means. While in some constructions the user has an option of mounting the imaging means onto a desired instrument place through dismantling and reassembling the instrument console, obviously this arrangement is not compatible with the normal operating routine of a dentist. Conventionally, the dedicated instrument connectors do not support any other instruments than the imaging means and, conversely, the imaging means cannot be connected to any other instrument connector. These dental units lack the means for identifying the type of attached instruments and controlling the dental unit on the basis of such identification signals. However, for the convenience of tie dental unit user it would be optimal to have all the required dental instruments to be quickly and effortlessly connectable to any desired instrument connector and, moreover, in any desired order—meaning that the dental unit should be equipped with general-purpose instrument connectors to which a camera or other dental accessory can be attached as desired. Particularly in dental clinics in which a greater number of dentists than one use the same dental unit alternately and each dentist desires to organize the order of their own instruments according to a preferred operating convenience, said novel type of dental unit facility is considered most welcome.

From patent publications EP 479 868, EP 110 200 and JP 192 3861, it is known to provide dental units with codable quick-connect connectors in which onto the connector pins can be switched the different physical parameters required to steer the instruments according to the operating situation. However, these prior-art dental units have not been equipped with facilities for connecting also an imaging means to such an instrument connector and for transferring the image signal via the instrument connector.

OBJECTS AND SUMMARY OF THE INVENTION

It is an object of the present invention to eliminate the above-mentioned drawbacks by virtue of providing a novel technique of connecting dental instruments to a dental unit.

It is a further object of the present invention to provide a novel connection technique of dental instruments by virtue of which method a dental unit can identify an imaging means or other dental instrument attached to a given instrument connector thereof and then switching the parameters and signals required for the control of said dental instrument to pass via said instrument connector of the dental unit.

It is still a further object of the present invention to provide a new type of imaging means such as an intraoral camera with advantageous properties suited for use in the above-described environment, whereby said imaging means does not require a separate base unit, but instead can be connected directly to a dental unit thus utilizing the existing functions of the dental unit.

It is a particular object of the invention to provide such an imaging means connection on a dental unit that, by virtue of said connection, to one and the same instrument connector can be attached either an imaging means or any other type of dental instrument, whereby all the instrument connectors of the dental unit can be equipped with said type of connection suitable for connecting different kinds of instruments thereto.

To achieve the above-described goals and others to be mentioned later in the text, the imaging means, dental unit and method according to the invention for connecting an imaging means to a dental unit are characterized by what is stated in the appended claims.

The benefits of the invention include that, in the combination of an imaging means with a dental unit according to the invention, the imaging camera can utilize the resources of the dental unit such as electricity, water, compressed air, control electronics and the instrument connectors themselves that are already provided for the needs of other dental instruments. According to the invention, the dental unit identifies the instrument attached to the instrument connector and switches thereon the physical variables required for any particular instrument function. As a further benefit of the invention may be mentioned that, via the instrument connector according to the invention, the dental unit can receive information variables such as a video signal and perform further transfer thereof to, e.g., a display device.

For the identification of instruments, the specific identification signal can be generated with the help of any conventional coding technique based on such elements as resistors, switches, etc. adaptable to function in conjunction with the instrument connector. Thus, the invention makes it possible to configure the imaging means with its connections, power feed and cooling medium circulation in a manner which is substantially more advantageous than prior-art combinations based on separate devices and control Systems. A still further benefit is that the dental unit may initially be equipped with a facility for connecting an imaging means, whereby the means such as a video camera itself be acquired later. Hence, a single camera can be swapped between a plurality of compatible dental units, whereby a dentist may operate in a number of separate dental units a single set of instruments, typically owned by the dentist him/herself. The dental unit can be furnished with such instrument connectors that any type of instrument can be attached to any instrument connector provided with, e.g., a conventional multiplex interface. Alternatively, one or some instrument connectors may be exclusively assigned to serve a given instrument or a plurality thereof.

The imaging means arrangement according to the invention is essentially characterized in that the object illumination system of the camera is adapted into the hand-piece portion of such an instrument. In the present arrangement, the light need not be conveyed over a long path, whereby light transmission losses are reduced and the thick light guide can be omitted from the instrument cable.

An intraoral camera implemented according to the invention does not require a separate base unit, but instead, the camera can be integrated with a conventional dentist's dental unit. Thus, the intraoral camera may be designed into a miniature device that is readily available in parallel with other dental instruments. The electrical supply and cooling medium of the intraoral camera can be furnished from the dental unit.

BRIEF DESCRIPTION OF THE DRAWINGS

In the following, the invention is described in greater detail with reference to preferred embodiments thereof having a nonlimiting character to the scope and spirit of the invention that are illustrated in the appended drawings in which.

DETAILED DESCRIPTION OF THE INVENTION

Figure 1A:
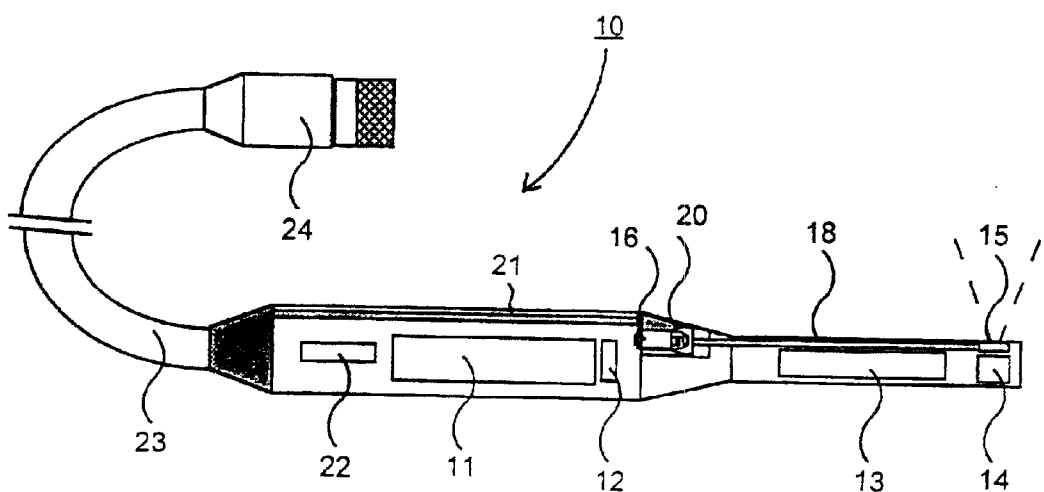
FIG. 1A shows an intraoral camera suitable for use in the invention.

Now referring to FIG. 1A, therein is shown an intraoral camera 10 housing a camera section 11, a light-sensitive image sensor element 12, an optical section 13, an image-orientation-mirroring element 14, a front-end optics section 15, a light source section 16, a cooling element 20, a light guide 18 and a sensor element 22. Additionally, the intraoral camera 10 includes an instrument connection cable 23 with a connector 24 placed at the other end of said cable.

During an imaging session, the illumination on the imaged object is furnished from the light source section 16 wherefrom the light travels along a light guide 18 to the front end of the intraoral camera 10. There, the light is launched via a plurality of exit points in order to obtain a maximally smooth illumination on the object to be imaged. Inasmuch the light source section 16 is thus located close to the exit point of object illumination, the length of the light guide 18 becomes so short that no substantial losses will occur over the transmission path of the illuminating light.

Figure 1B:
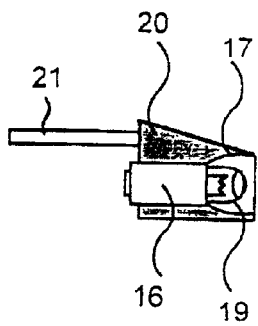
FIG. 1B shows the light source section of the intraoral camera illustrated in FIG. 1A.

The assembly of the light source 16 and elements enclosing the same is shown in greater detail in FIG. 1B. The front end of the light source 16 contains a condenser lens 19 and a reflector 17 surround the light source. The condenser lens 19 directs the object-illuminating light forward and the reflector 17 surrounding the light source gathers the light emitted by the light source with maximum efficiency thus reducing light losses and improving illumination intensity at the object.

The light source 16 can be implemented using a lamp of relatively low input power, whereby the heat of the lamp can be absorbed by a cooling element 20 surrounding the lamp. From the cooling element 20, the heat is removed by means of a cooling medium that in the exemplifying embodiment is compressed air available from the dental unit. The function of cooling by compressed air is to prevent the lamp heat from reaching the camera and its CCD image sensor that are located close to the lamp, because an elevated operating temperature of the camera would otherwise deteriorate the signal-to-noise ratio of the camera output signal.

The output intensity of the light source 16 can be adjusted by controlling the operating voltage of the lamp. This arrangement helps avoid situations causing saturation of the camera sensor and thus contributes to higher image quality.

The image of the object is projected onto the light-sensitive image sensor 12 of the camera over a path comprising the front-end optics 15, an optical image-mirroring element 14 and further the internal optical system 13 located in the front end of the intraoral camera 10. The optical image-mirroring element 14 flips the image orientation in a so-called penta prism that corrects the image orientation already before the image reaches the camera section 11 thus disposing with the need for coring the image orientation in the post-processing steps of the camera signal. The image focus is controlled with the help of the optical section 13 by adjusting a control knob (not shown in the diagram) placed on the intraoral camera head.

The optical section 13 may be implemented as a constant-magnification lens system or, alternatively, including a zoom facility.

The light-sensitive image sensor element 12 may be, e.g., a CCD-type solid-state camera sensor. The light-sensitive image sensor element 12 converts the optical image projected thereon into a video signal and transfers the signal to the camera section 11, wherefrom the outgoing video signal travels over a conductor of the instrument connection cable 23 to the cable connector 24. The camera section may be implemented using, e.g., a video camera, but also other type of imaging means is also feasible. The camera optics is provided with an adjustable aperture stop.

The intraoral camera 10 may include a sensor element 22 by means of which the dental unit can detect the removal of the intraoral camera 10 from its storage support, that is, the use thereof. Such a sensor element 22 can also be utilized to produce a signal on the return of the camera into its storage support, that is, on the end instant of camera use. Also other dental instruments can be equipped with a sensor element 22. This type of element 22 may be, e.g., a reed relay or a Hall sensor, both capable of being activated by a strong magnetic field. Besides being suitable for use in the instrument console proper of a dental unit, it can also be applied to separate storage racks which are placed apart from the instrument console of the dental unit. Such a separate rack can be placed in a desired location within the dentist's operating room.

The electrical supply of the intraoral camera and the cooling medium, advantageously compressed air, required for cooling the light source 16 are passed via the connector 24 and the instrument connection cable 23. The video signal is passed via the instrument connection cable 23 and the connector 24 to the dental unit 30. According to the invention, the connector 24 is of the same type as those of the other dental instruments attached to the dental unit 30.

Figure 2:
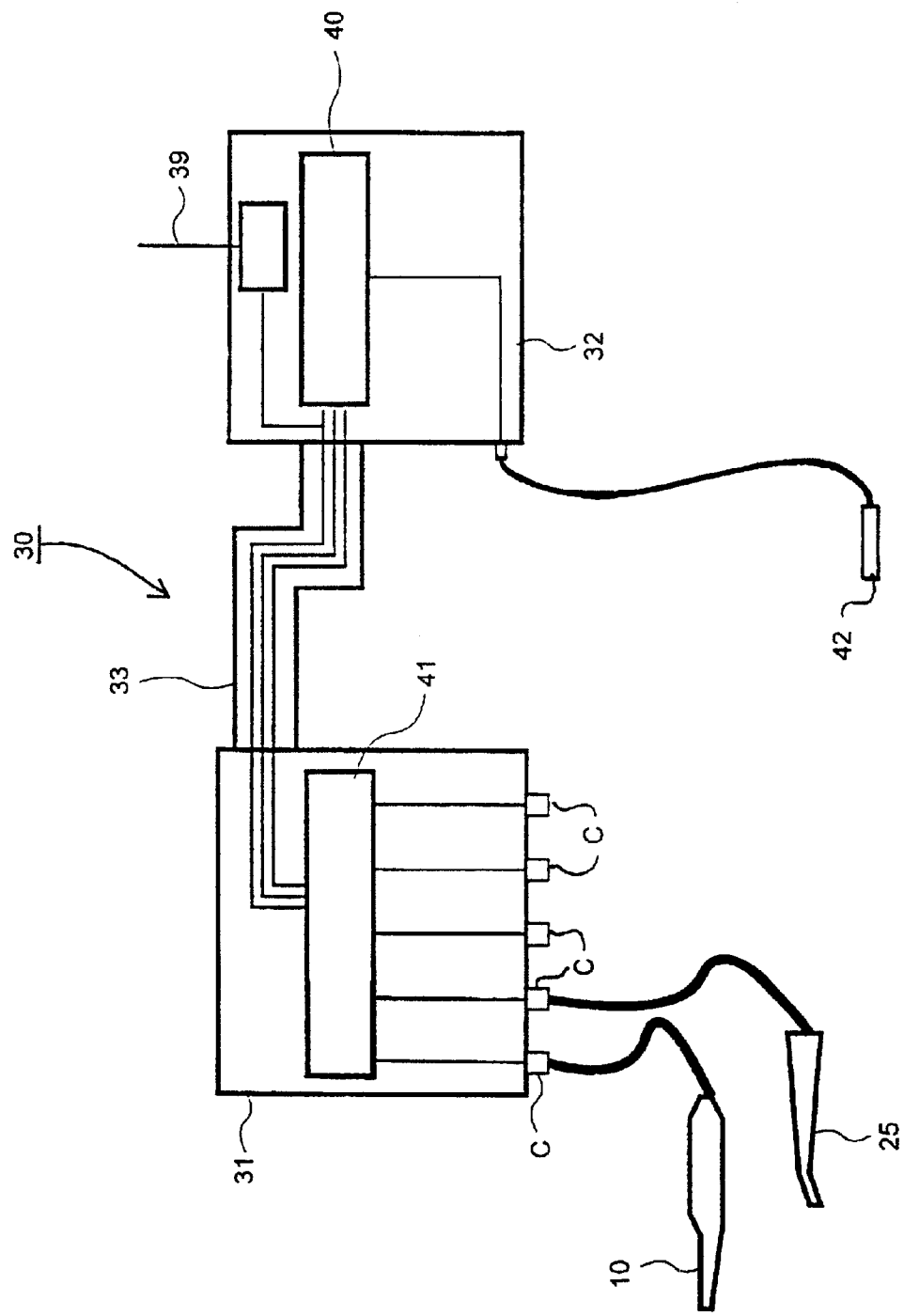
FIG. 2 shows a dental unit according to the invention having a plurality of dental instruments attached thereto.

In FIG. 2 is shown an embodiment of a dental unit 30 according to the invention. In the present context, the term dental unit is used in reference to a means, capable of having at least one instrument 25 attached thereto suitable for use in dental care and having facilities for feeding electrical supply, water and/or compressed air to said instruments 25. The dental unit 30 includes an instrument console 31, a body unit 32 and a cable conduit 33 joining these two. The cable conduit 33 is suitable for passing therethrough the electrical conductors, signal lines and the water/air supply hoses of the unit. The instrument console 31 contains an electronics unit 41 with fictions required for controlling the dental instruments. The body unit 32 contains an electronics unit 40 housed in the body unit, a connection for a foot control unit 42 and a video signal output 39.

The instrument console 31 of the dental unit 30 shown in FIG. 2 includes a plurality of mutually identical connectors C, suitable for connection of dental instruments 25 and the intraoral camera 10 according to the invention. Any instrument can be attached to any of the connectors C. In the illustrated embodiment of the dental unit, thereto is connected an intraoral camera 10 and a dental instrument 25. The dental instrument 25 may contain, e.g., a turbine or micromotor. The dental unit 30 identifies each instrument 10,25 being attached thereto and the electronics unit 41 of the dental unit 30 controls the physical operating parameters according to the needs of each instrument 10,25. For instance, when the intraoral camera 10 is being used, the supply voltage and cooling medium required thereto can be controlled to correct values and the image information signal produced by the camera is switched to the output 39.

The instrument being used can be controlled by means of a foot control unit 42 placed on the floor. As the dental unit 30 is aware of the type of instrument 10, 25 being used, the unit can convert the signals issued with the foot control unit 42 into correct command signals to control said instrument 10,25 in particular. An example of such use of the foot control unit 42 is a situation in which the intraoral camera 10 is in use and the foot control unit 42 can be activated to make the camera record a still picture.

According to the invention, the operation of the imaging means 10, the instruments 25 and the foot control unit 42 is advantageously steered via the operator interface of the dental unit 30.

A preferred arrangement according to the invention is to equip all the connector positions C with the universal interface connector with the exception of one connector that is left for a specific use serving only the syringe.

Figure 3:
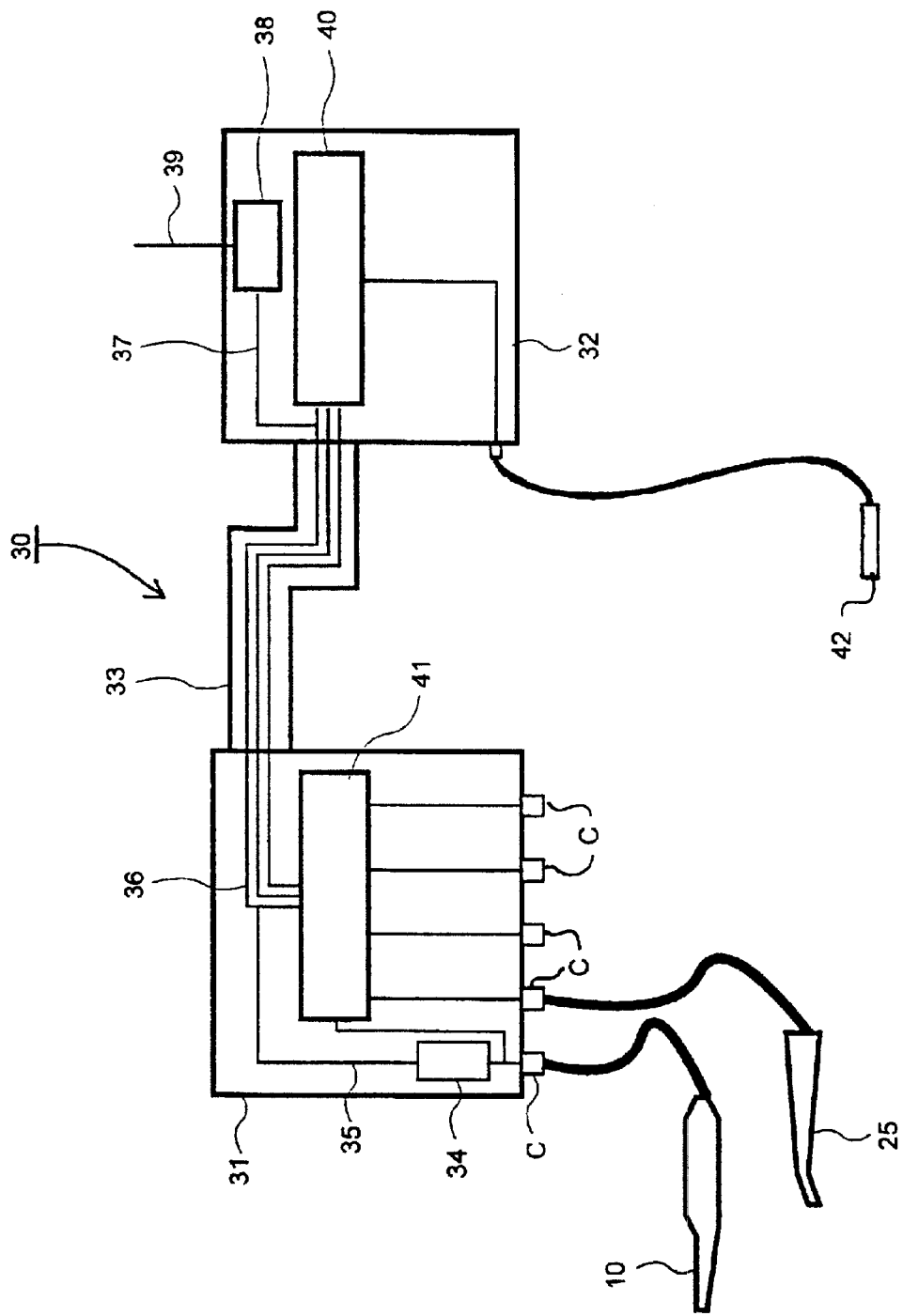
FIG. 3 shows a preferred technique of transferring the image information signal through the dental unit.

In FIG. 3 is shown a possible arrangement for passing the image information signal through the dental unit 30 up to the signal output 39. In this embodiment, only the most lateral instrument connector C is equipped suitable for accepting both the imaging means 10 as well as other types of instruments 25. The signal produced by the imaging means 10 is passed via the instrument cable 23, its connector 24 and the connector C of the dental unit 30 to the circuitry of the dental unit 30. In this chain, the signal is first passed to a modulator 34 wherein it is upconverted to a higher carrier frequency. The modulated signal is taken over a conductor 35 to a cable 36 which is primarily adapted to serve a different task as, e.g., an electric supply cable. However, passing the modulated video signal simultaneously along a cable 36 serving a duty does not interfere with the primary function of the cable 36. Transmission of the image information signal in this manner is an advantageous arrangement inasmuch it disposes with the need for installing a sate auxiliary cable in the already crammed conductor conduit 33. The modulated signal is next passed in the conductor conduit 33 between the instrument console 31 and the body unit 32 to the interior of the body unit 32, where the modulated signal is passed over a conductor 37 to a demodulator 38. Therefrom the signal is further passed to the video signal output 39, and therefrom to, e.g., a video monitor for display and/or to a storage means.

Figure 4:
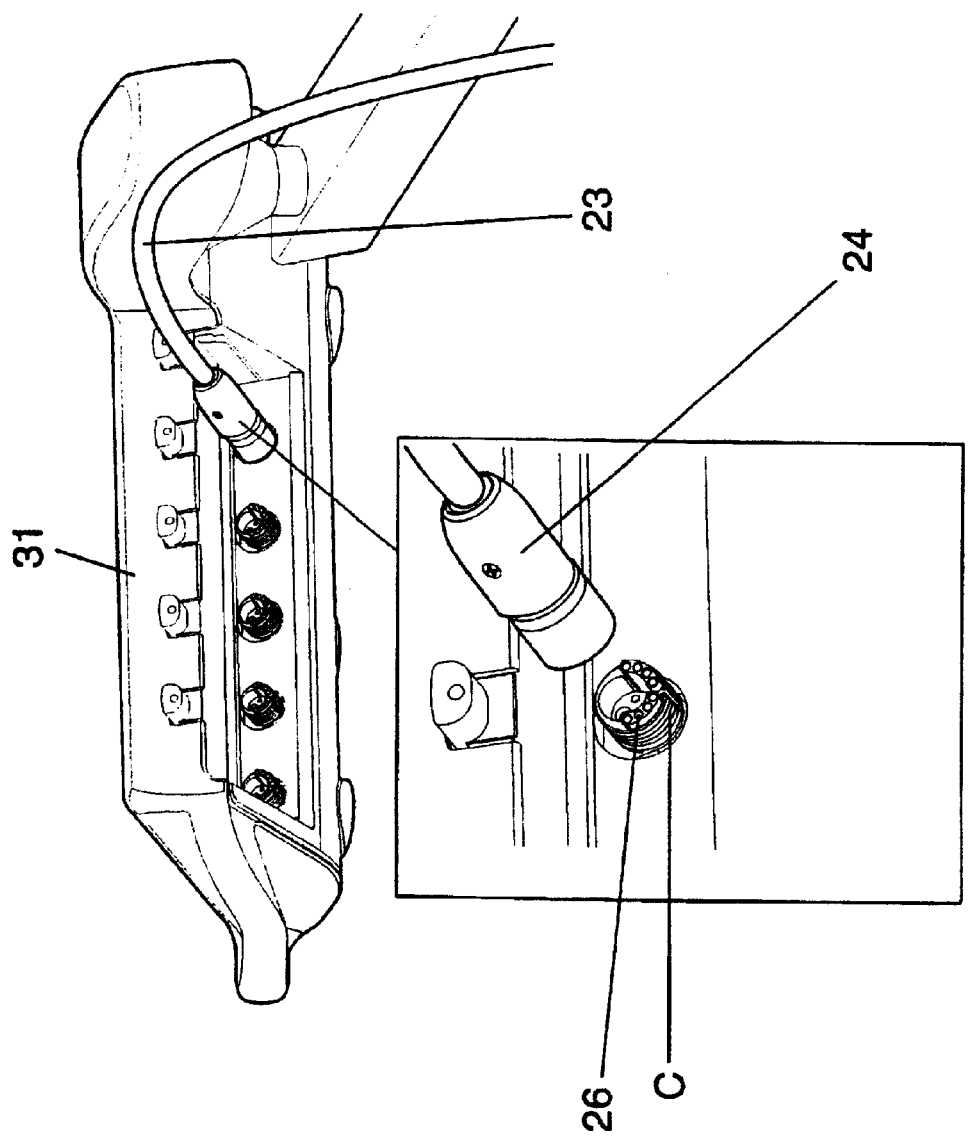
FIG. 4 shows a connector arrangement according to the invention equipped with an instrument-identifying facility.

In FIG. 4 is shown a possible connector construction according to the invention. It must noted that the identification of an instrument in accordance with the invention need not, within the scope and spirit of the invention, be necessarily implemented using the technique described herein, but any other corresponding embodiment can be employed as well. As shown in FIG. 4, the quick-connect connector 24 of the instrument connection cable 23 of the imaging means 10 or any other dental instrument 25 is attached to an instrument connector C according to the invention on the instrument console 31 of the dental unit 30. Herein, e.g., one of the connector pins 26 is connected to communicate with means serving to identify the instrument 10,25 attached to said instrument connector C. This kind of identification may be based on, e.g., a resistor of a specific resistance which is placed in the connector 24 so as to communicate with such a connector pin 26' (not shown in the diagram) of the connector 24 that upon the mating of the connector 24 with the instrument connector C meets said instrument-identifying connector pin 26. As the dental unit 30 thus identifies the specific type of instrument 10, 25 attached to said instrument connector C, it can correctly switch the specific physical variables required by said instrument 10, 25 to be available at said instrument connector C.

In the embodiment shown in FIG. 4, the video signal can be passed to the dental unit 30 via any of the connector pins 26. Particularly according to the invention, it is possible to utilize the individual connectors pins 26 for transferring different types of signals as required by the actual operating situation and/or to adapt an individual connector pin 26 for simultaneous transfer of a plurality of signals modulated to different carrier frequencies.

The above-given description must be understood to represent only a few preferred embodiments of the invention whose details may be varied within the scope and spirit of the invention. For instance, techniques different from those employed in the above examples for transferring the image information signal from the instrument connector to the display and/or image storage device may be contemplated. The scope of the invention is defined in the appended claims.

What is claimed is:

1. An imaging apparatus comprising:
   an image recording device;
   an illumination system;
   a plurality of optical elements;
   an instrument connection cable;
   a connector;
   wherein said apparatus is structured and arranged to be connectable to an instrument connector of a dental unit via said instrument cable and said connector; and
   wherein at least a portion of a plurality of operating variables for said apparatus are available from said dental unit; and
   wherein said apparatus is adapted to produce a signal to be passed to one of a display and image recording device; and
   wherein said apparatus is structured and arranged so that upon connection of said connector to said dental unit said apparatus produces a identification signal and transmits said signal to said dental apparatus, said identification signal being adapted to inform said dental unit of the connection of said apparatus to said unit and provide information to said unit as to the physical variables required for the operation of said apparatus.

2. The imaging apparatus according to claim 1, wherein said connector is structured and arranged to be receivable by conventional multiplex connection.

3. The imaging apparatus according to claim 1, wherein said illumination system is structured and arranged to be cooled by a cooling medium.

4. The imaging apparatus according to claim 3, wherein said cooling medium is transferred from said dental unit to said illumination system via an instrument connection cable.

5. The imaging apparatus according to claim 1, wherein a light source of said illumination system is surrounded by a reflective material in order to maximize an output of said light source.

6. The imaging apparatus according to claim 1, wherein said illumination system comprises a light source having an adjustable light output.

7. A dental unit comprising:
   at least one instrument connector structured and arranged to connect with both one of a plurality of different dental instruments and a imaging apparatus;
   means for identifying a specific one of said plurality of dental instruments and imaging apparatus connected to said instrument connector based on a instrument specific connection signal generated at said instrument connection;
   means for activating and transferring to said instrument connector the specific physical variable required for the operation of said specific one of said plurality of dental instruments and imaging apparatus.

8. The dental unit according to claim 7, wherein a connection of one of said plurality of different dental instruments and said imaging apparatus with said at least one instrument connector forms a conventional multiplex connection.

9. The dental unit according to claim 7, wherein said at least one instrument connector comprises a plurality of instrument connectors.

10. The dental unit according to claim 7, wherein said dental unit is structured and arranged to be operable connected with a imaging apparatus comprising an image recording device; an illumination system; a plurality of optical elements; an instrument connection cable; connector; wherein said imaging apparatus is structured and arranged to be connectable to said dental unit via said instrument cable and said connector; and wherein at least a portion of a plurality of operating variables for said apparatus are available from said dental unit; and wherein said imaging apparatus is adapted to produce a signal to be passed to one of a display and image recording device; and wherein said apparatus is structured and arranged so that upon connection of said connector to said dental unit said apparatus produces a identification signal and transmits said signal to said dental unit, said identification signal being adapted to inform said dental unit of the connection of said apparatus to said unit and provide information to said unit as to the physical variables required for the operation of said apparatus.

11. The dental unit according to claim 7, further comprising an operator interface adapted for controlling said imaging apparatus.

12. The dental unit according to claim 7, wherein said unit comprises a modulator and demodulator adapted for processing an image information signal and means for transmitting said signal in a modulated form.

13. The dental unit according to claim 7, wherein said at least one instrument connector comprises a plurality of connector pins wherein said pins are adapted for transmitting a plurality of different signals required for said plurality of dental instruments and said imaging apparatus and said pins are adapted for transmitting a plurality of signals modulated to different carrier frequencies.

14. The dental unit according to claim 7, further comprising an instrument console structured and arranged for holding said plurality of dental instruments and said imaging apparatus and means for sensing the removal of one of said plurality of dental instruments and said imaging apparatus for use.

15. The dental unit according to claim 7, wherein said one of said plurality of different dental instruments and said imaging apparatus contain a sensor element, said sensor element comprising one of a reed relay and a hall sensor, said sensor element adapted to issue a single corresponding to a beginning and an ending of use of said one of said plurality of different dental instruments and said imaging apparatus.

16. The dental unit according to claim 7, further comprising means for switching onto said at least one instrument connector a physical variable required for use of said one of said plurality of different dental instruments and said imaging apparatus when said one of said plurality of different dental instruments and said imaging apparatus is taken for use and said means for switching adapted to switch said physical variable off when the use of said one of said plurality of different dental instruments and said imaging apparatus has ceased.

17. A method of connecting an imaging apparatus to a dental unit comprising the steps of:

attaching said imaging apparatus to said dental unit by inserting an instrument connection connector of said imaging apparatus into one of a plurality of instrument connection connectors arranged in said dental unit, said instrument connection connectors being structured and arranged to receive one of said imaging apparatus and one of a plurality of different dental instruments;

identifying the attachment of said imaging apparatus to said instrument connection connector;

forwarding to said instrument connector a specific physical variable required for operating said imaging apparatus.

18. The method according to claim 17, wherein said specific physical variable is forwarded via connector pins of said instrument connector.

19. The method according to claim 18, wherein different types of signals are passed via said connector pins.

20. The method according to claim 19, wherein via a single connector pin are passed signals modulated to different carrier frequencies.

21. The method according to claim 17, further comprising the step of controlling the operation of said imaging apparatus via an operator interface of said dental unit.

* * * * *